(12) United States Patent
Lindberg et al.

(10) Patent No.: US 11,013,744 B2
(45) Date of Patent: *May 25, 2021

(54) [6R]—MTHF—AN EFFICIENT FOLATE ALTERNATIVE IN 5-FLUOROURACIL BASED CHEMOTHERAPY

(71) Applicant: Isofol Medical AB, Gothenburg (SE)

(72) Inventors: Per L. Lindberg, Gothenburg (SE); Anders Vedin, Gothenburg (SE); Gunnel E. Sundén, Gothenburg (SE); Bengt Gustavsson, Västra Froelunda (SE)

(73) Assignee: Isofol Medical AB, Gothenburg (SE)

( * ) Notice: Subject to any disclaimer, the term of this patent is extended or adjusted under 35 U.S.C. 154(b) by 120 days.

This patent is subject to a terminal disclaimer.

(21) Appl. No.: 15/865,870

(22) Filed: Jan. 9, 2018

(65) Prior Publication Data
US 2019/0060316 A1 Feb. 28, 2019

(30) Foreign Application Priority Data

Aug. 24, 2017 (EP) .................................. 17187684

(51) Int. Cl.
*A61K 31/519* (2006.01)
*A61P 35/00* (2006.01)
*A61K 9/00* (2006.01)
*A61K 31/282* (2006.01)
*A61K 31/4545* (2006.01)
*A61K 31/4745* (2006.01)
*A61K 31/513* (2006.01)
*A61K 31/555* (2006.01)
*A61K 39/395* (2006.01)
*A61K 39/00* (2006.01)
*C07K 16/22* (2006.01)

(52) U.S. Cl.
CPC .......... *A61K 31/519* (2013.01); *A61K 9/0019* (2013.01); *A61K 31/282* (2013.01); *A61K 31/4545* (2013.01); *A61K 31/4745* (2013.01); *A61K 31/513* (2013.01); *A61K 31/555* (2013.01); *A61K 39/395* (2013.01); *A61K 39/39558* (2013.01); *A61P 35/00* (2018.01); *A61K 2039/505* (2013.01); *A61K 2039/545* (2013.01); *C07K 16/22* (2013.01)

(58) Field of Classification Search
CPC .................................................. A61K 31/519
See application file for complete search history.

(56) References Cited

U.S. PATENT DOCUMENTS

| 5,376,658 A | 12/1994 | Spears et al. |
| 5,534,519 A | 7/1996 | Spears et al. |
| 7,799,782 B2 | 9/2010 | Munson et al. |
| 9,675,617 B2 | 6/2017 | Gustavsson et al. |
| 2015/0017158 A1 | 1/2015 | Gustavsson et al. |

FOREIGN PATENT DOCUMENTS

| EP | 3305318 A1 | 4/2018 |
| JP | 2010-503717 | 2/2010 |
| JP | 2012-503639 | 2/2012 |
| JP | 2015-504079 | 2/2015 |
| JP | 2016-040269 | 3/2016 |
| KR | 1020070019725 A | 2/2007 |
| WO | WO-2005/097086 A2 | 10/2005 |
| WO | WO-2007/064968 A2 | 6/2007 |
| WO | WO-2008109349 A1 | 9/2008 |

OTHER PUBLICATIONS

Notification of Transmittal, International Search Report, and Written Opinion, dated May 13, 2019 in PCT/IB2019/000008.
K.M. Li et al., "Altered deoxyuridine and thymidine in plasma following capecitabine treatment in colorectal cancer patients," 63(1) Br. J. Clin. Pharmacol. 67-74 (2007) (published online Jul. 7, 2006. doi: 10.1111/j.1365-2125.2006.02710.x).
E. Odin et al., "Simultaneous quantification of deoxyuridine, fluorodeoxyuridine and 5-fluorouracil in plasma samples by using a LC-MS/MS method," 51(Supp. 3) Eur. J. Cancer S93 (2015) (abstract and poster).
C.P. Spears et al., "Rapid and complete thymidylate synthase (TS) inhibition in tumors after fluorouracil (5-FU) by methylenetetrahydrofolate (ch2fh4) preloading," 38(Supp. 7) Eur. J. Cancer S22 (2002).
Saif et al., "Phase III Multicenter Randomized Clinical Trial to Evaluate the Safety and Efficacy of CoFactor/5-Fluorouracil/Bevacizumab Versus Leucovorin/5-Fluorouracil/Bevacizumab as Initial Treatment for Metastatic Colorectal Carcinoma," Clinical Colorectal Cancer, vol. 6, No. 3, 229-234 (2006).
Extended European Search Report dated Nov. 29, 2017, issued in Application No. 17187684.0.
Extended European Search Report dated Nov. 29, 2017, issued in Application No. 17187682.4.
G. Carlsson et al., Cancer Journal, vol. 10 No. 5, pp. 266-273 (1997).
Osamu Shinto et al., CAS: 154:351367 (2010).
Bengt Gustavsson et al., "Phase 1 dose de-escalation trial of the endogenous folate [6R]-5,10-methylene tetrahydrofolate in combination with fixed-dose pemetrexed as neoadjuvant therapy in patients with resectable rectal cancer," Investigational New Drugs, vol. 33, No. 5, pp. 1078-1085 (2015).
Yvonne Wettergren et al., "A pharmacokinetic and pharmacodynamic investigation of Modufolin® compared to Isovorin® after single dose intravenous administration to patients with colon cancer: a randomized study," Cancer Chemotherapy and Pharmacology, vol. 75, No. 1, pp. 37-47 (2015).

(Continued)

Primary Examiner — Kortney L. Klinkel
Assistant Examiner — Tori Strong
(74) Attorney, Agent, or Firm — Covington & Burling, LLP; Einar Stole; Priscilla G. Dodson

(57) ABSTRACT

The present invention relates to the treatment of solid tumors in humans such as cancer, especially colorectal cancer (CRC), which involves administering the diastereomerically pure folate adjuvant [6R]-5,10-methylenetetrahydrofolate in 5-fluorouracil (5-FU) based chemotherapy.

15 Claims, 4 Drawing Sheets

(56) References Cited

OTHER PUBLICATIONS

Figure 1:
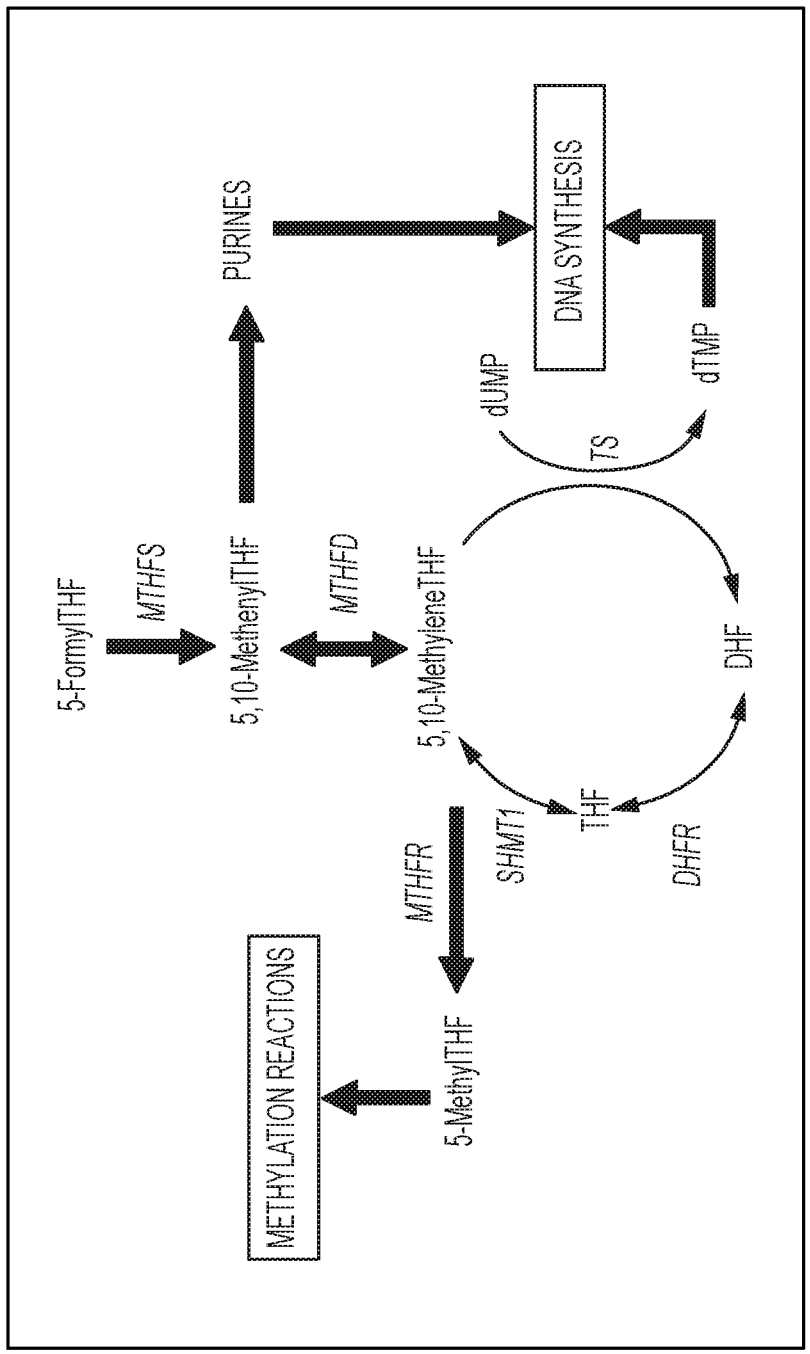

Isofol Medical Ab, "Modufolin in Combination with 5-Fluorouracil Alone or Together with Oxaliplatin or Irinotecan in Colorectal Cancer," ClinicalTrials.gov, pp. 1-4 (Jan. 11, 2017).
Notification of Transmittal, International Search Report, and Written Opinion, issued Jul. 30, 2018 in PCT/IB2018/000206.
Peter V. Danenberg et al., "Folates as adjuvants to anticancer agents: Chemical rationale and mechanism of action," Critical Reviews in Oncology /Hematology, vol. 106, pp. 118-131 (2016).
Hafström LO, Carlsson G. et al., "5-fluorouracil (5-FU) and 5,10-methylene Tetrahydrofolate (5,10-CH2FH4) as Adjuvant Therapy in an Experimental Rodent Colon Carcinoma Model," Europe PMC, 1997, 17, 3671-3674, (Sep. 1, 1997).
"Modufoline® in Combination With 5-Fluorouracil Alone or Together With Oxaliplatin or Irinotecan in Colorectal Cancer," ClinicalTrials.gov, (Apr. 1, 2020).
Korean Search Report for Application No. 10-2019-7001570 (dated Jun. 23, 2020).
B. Glimelius et al., "A randomized phase III multicenter trial comparing iinotecan in combination with the Nordic bolus 3-FU and folnic avidi schedule or the bolus/infused de Gramont schedule (Lv5FU2) in patients with metastatic colorectal cancer," 19(5) Annals of Oncology (May 2008).
H. Sørbye et al., "Multicecnter Phase II Study of Nordic Fluorouracil and Folnic Acid Bolus Schedule Combined with Oxaliplatin As First-Line Treatment of Metastatic Colorectal Cancer," 22(1) Journal of Clinical Oncology 31-38, (Jan. 1, 2004).
P. Larsson et al.. "A Pharmacokinetic Study of 5-FU/Leucovorin and Alpha-Interferon in Advanced Cander," 39 Acta Oncologica 59-63 (2000).
Ford et al. Patterns of elevation of plasma 2'-deoxyuridine, a surrogate marker of thymidylate synthase (TS) inhibition, after administration of two different schedules of 5-fluorouracil and the specific TS inhibitors raititrexed (Tomudex) and zd93311 //Clinical Cancer Research, 8(1):103-109, (Jan. 2002).
Halfdan Sørbye and Olav Dahl; "Nordic 5- fluorouracil/leucovorin bolus schedule combined with oxaliplatin (Nordic FLOX) as first-line treatment of metastatic colorectal cancer", Acta Oncologica, 42(8): 827-831, (2003).
Yu-Ping Un, "Pharmacotherapy of colorectal cancer", The Journal of Taiwan Pharmacy, 30(3): 86-91, (Sep. 30, 2014).
"Modufolin in Combination with 5-Fluorouracil Alone or Together with Oxaliplatin or irinotecan in Colorectal Cancer," ClinicalTrials.gov (Mar. 8, 2017).

| PATIENT NO | TREATMENT LINE | DOSES | | | | RESPONSE RATE acc TO RECIST 1.1 AFTER 8 WEEKS | RESPONSE RATE acc TO RECIST 1.1 AFTER 16 WEEKS |
| --- | --- | --- | --- | --- | --- | --- | --- |
| | | [6R]-MTHF mg/m² | 5-FU mg/m² | OXALIPL-ATIN mg/m² | IRINOTE-CAN mg/m² | | |
| 1 | 1 | 2×30 | 2×500 | - | - | 0,00 | - |
| 2 | 1 | 2×30 | 2×500 | - | - | -13,97 | - |
| 3 | 1 | 2×30 | 2×500 | - | - | -27,27 | - |
| 4 | 1 | 2×60 | 2×500 | - | - | 7,02 | -14,04 |
| 5 | 1 | 2×60 | 2×500 | - | - | 1,92 | 0,00 |
| 6 | 3 | 2×120 | 2×500 | - | - | 30,77 | - |
| 7 | 3 | 2×120 | 2×500 | - | - | -2,15 | - |
| 8 | 3 | 2×120 | 2×500 | - | - | 6,03 | 22,41 |
| 9 | 2 | 2×240 | 2×500 | - | - | 19,35 | 38,71 |
| 10 | 1 | 2×240 | 2×500 | - | - | -51,22 | -51,22 |
| 11 | 2 | 2×240 | 2×500 | - | - | -21,43 | - |
| 12 | 2 | 2×30 | 2×500 | 85 | - | -17,98 | - |
| 13 | 2 | 2×30 | 2×500 | 85 | - | -6,85 | -6,85 |
| 14 | 2 | 2×30 | 2×500 | 85 | - | -27,27 | - |
| 15 | 2 | 2×60 | 2×500 | 85 | - | -41,86 | -18,6* |
| 16 | 3 | 2×60 | 2×500 | 85 | - | -20,51 | - |
| 17 | 2 | 2×60 | 2×500 | 85 | - | -4,55 | - |
| 18 | 1 | 2×60 | 2×500 | 85 | - | -40,00 | -42,50 |
| 19 | 3 | 2×60 | 2×500 | 85 | - | -12,70 | - |
| 20 | 3 | 2×30 | 2×500 | 85 | - | 26,00 | - |
| 21 | 1 | 2×30 | 2×500 | - | 180 | -41,86 | - |

FIG. 2

| 22 | 2 | 2×30 | 2×500 | - | 180 | 14,30 | - |
| 23 | 1 | 2×30 | 2×500 | - | 180 | 0,00 | 3,18 |
| 24 | 5 | 2×30 | 2×500 | - | 180 | -6,56 | - |
| 25 | 3 | 2×60 | 2×500 | - | 180 | 18,07 | - |
| 26 | 2 | 2×60 | 2×500 | - | 180 | 60,38 | - |
| 27 | 1 | 2×60 | 2×500 | - | 180 | -88,33 | -86,67 |
| 28 | 1 | 1×60[1] | 1×400 2400[2] | 85 | - | -31,58 | -31,58 |
| 29 | 1 | 1×60[1] | 1×400 2400[2] | 85 | - | -38,46 | -60,44 |
| 30 | 2 | 1×60[1] | 1×400 2400[2] | 85 | - | -44,74 | -56,14 |
| 31 | 2 | 1×120[3] | 1×400 2400[2] | 85 | - | *) | - |
| 32 | 2 | 1×120[3] | 1×400 2400[2] | 85 | - | 13,95 | - |
| 33 | 2 | 1×120[3] | 1×400 2400[2] | 85 | - | *) | - |
| 35 | 2 | 1×120[3] | 1×400 2400[2] | 85 | - | *) | - |
| 36 | 2 | 1×120[3] | 1×400 2400[2] | 85 | - | -1,14 | - |
| 37 | 2 | 1×120[3] | 1×400 2400[2] | 85 | - | 0,00 | - |
| 38 | 2 | 1×120[3] | 1×400 2400[2] | 85 | - | -8,57 | - |

NOTE: [1] DIVIDED INTO 2 SEPARATE BOLUS DOSES OF 30 mg ON DAY 1, [2] 46 HOURS INFUSION
[3] DIVIDED INTO 2 SEPARATE BOLUS DOSES OF 60 mg ON DAY 1, [4] + BEVACIZUMAB (5mg/kg)
*) THE APPEARANCE OF ONE OR MORE LESIONS IS CONSIDERED PROGRESSIVE DISEASE

FIG. 2
CONTINUED

|  | CoFactor/<br>5-FU<br>(n=147) | LEUCOVORIN<br>/5-FU<br>(n= 148) | P-VALUE |
|---|---|---|---|
| PATIENTS REPORTING AT LEAST 1 HEMATOLOGICAL OR GASTROINTESTINAL ADVERSE EVENT OF GRADE 3 OR GREATER | 23 | 10 | p< 0.05 |
| HEMATOLOGICAL | 11 | 7 |  |
| GASTROINTESTINAL | 12 | 5 |  |

ADVENTRX PHARMACEUTICALS

|  | CoFactor/<br>5-FU<br>(n=150) | LEUCOVORIN<br>/5-FU<br>(n= 150) |
|---|---|---|
| OBJECTIVE RESPONSE RATE | 10.7% | 13.3% |
| MEDIAN PROGRESSION-FREE SURVIVAL (MONTHS) | 6.3mo | 6.1mo |
| PRELIMINARY MEDIAN SURVIVAL (MONTHS) | 14.7mo | 14.3mo |

FIG. 3

[6R]—MTHF—AN EFFICIENT FOLATE ALTERNATIVE IN 5-FLUOROURACIL BASED CHEMOTHERAPY

FIELD

The present invention relates to the treatment of solid tumors in humans such as cancer, which involves [6R]-5,10-methylenetetrahydrofolate ([6R]-MTHF) in 5-fluorouracil (5-FU) based chemotherapy.

BACKGROUND OF THE INVENTION 5-fluorouracil (5-FU) was first introduced in 1957, and still remains an essential part of the treatment of a wide range of solid tumours such as breast tumours, tumours of head and neck and gastrointestinal tumours.

5-FU is an example of a rationally designed anticancer agent. Observations of utilization of uracil in rat liver tumours indicated that the utilization of this nucleobase (there are four nucleobases in the nucleic acid of RNA) [Berg J M; Tymoczko J L; Stryer L (2002). Biochemistry (5th ed.), WH Freeman and Company. pp. 118-19, 781-808. ISBN 0-7167-4684-0. OCLC 179705944] was more pronounced in the tumours than in non-malignant tissue. This implicated that the enzymatic pathways for uracil utilization differs between malignant and normal cells [Rutman R J et al. Studies in 2-acetylaminofluorene carcinogenesis. III. The utilization of uracil 2-$^{14}$C by preneoplastic rat liver and rat hepatoma. Cancer Res 1954; 14: 119-123]. 5-FU was then synthesized as an antimetabolic agent [Heidelberger C et al. Fluorinated pyrimidines, a new class of tumour-inhibitory compounds. Nature 1967; 179: 663-666]. In 5-FU, the hydrogen atom in position 5 of uracil is replaced by the similar sized atom of fluorine, and 5-FU was designed to occupy the active sites of enzymes, blocking the metabolism of malignant cells.

The overall response rate of 5-FU alone is quite limited, reaching levels of 10-15% [Johnston P. G., Kaye S. Capcetabine; a novel agent for the treatment of solid tumours. Anticancer Drugs 2001, 12: 639-646] and modulation strategies to increase the anticancer activity of 5-FU have been developed. One of the most widely used strategies is a co-administration of Leucovorin, the calcium salt of folinic acid. Leucovorin (LV) acts as a stabiliser of the ternary complex, a structure formed by[1] 5,10-methylene tetrahydrofolate, the active metabolite of LV, of[2] FdUMP, the 5-FU active metabolite and of[3] Thymidylate synthase. This ternary complex inhibits the enzyme thymidylate synthase, an enzyme necessary for DNA synthesis [Longley D. B. et al. 5-Fluorouracil. Mechanisms of action and clinical strategies, Nat Rev Cancer. 2003 May; 3(5):330-8. Review]. By adding LV to 5-FU the overall response rates increased to over 20% [Longley D. B. et al. 2003 ibid.].

Breast cancer is the most frequently diagnosed cancer and the leading cause of cancer-related death among females worldwide (Breast Cancer, http://www.cancerresearchuk.org/cancer-info/cancerstats/world/breast-cancer-world/). Despite the gains in early detection, up to five percent of women diagnosed with breast cancer in the United States have metastatic disease at the time of first presentation. In addition, up to 30 percent of women with early-stage, non-metastatic breast cancer at diagnosis will develop distant metastatic disease [Early Breast Cancer Trialists' Collaborative Group (EBCTCG). Effects of chemotherapy and hormonal therapy for early breast cancer on recurrence and 15-year survival: an overview of the randomised trials. Lancet 2005; 365:1687]. Although metastatic breast cancer is not curable, meaningful improvements in survival have been seen, coincident with the introduction of newer systemic therapies see [Chia S. K., Speers C. H., D'yachkova Y. et al. The impact of new chemotherapeutic and hormone agents on survival in a population-based cohort of women with metastatic breast cancer. Cancer 2007; 110:973] and [Gennari A., Conte P., Rosso R. et al. Survival of metastatic breast carcinoma patients over a 20-year period: a retrospective analysis based on individual patient data from six consecutive studies. Cancer 2005; 104:1742] and [Dafni U., Grimani I., Xyrafas A. et al. Fifteen-year trends in metastatic breast cancer survival in Greece. Breast Cancer Res Treat 2010; 119:621].

The goals of treatment of metastatic breast cancer are to prolong survival and improve quality of life by reducing cancer-related symptoms. Cytotoxic chemotherapy (including the use of 5-FU) is particularly used in patients with hormone receptor-negative patients, patients with symptomatic hormone-receptor and a rapid disease progression or a large tumour burden involving visceral organs [Wilcken N., Hornbuckle J., Ghersi D.; Chemotherapy alone versus endocrine therapy alone for metastatic breast cancer. Cochrane Database Syst Rev 2003; :CD002747]. 5-FU is usually combined with cyclophosphamide and methotrexate (CMF). The reponse rate is around 20% and the OS around 20 months [Stockler M. R., Harvey V. J., Francis P. A. et al. Capecitabine versus classical cyclophosphamide, methotrexate, and fluorouracil as first-line chemotherapy for advanced breast cancer. J Clin Oncol 2011; 29:4498].

5-FU is also used for the treatment of advanced and recurring head and neck squamous cell cancer. The prognosis in this patient group is generally poor with a median survival time in most studies of 6-9 months. 5-FU is mainly used in combination therapies with platinum compounds. Response rates are around 30% but the survival time remains low, around 6 months see [Clavel M., Vermorken J. B., Cognetti F. et al. Randomized comparison of cisplatin, methotrexate, bleomycin and vincristine (CABO) versus cisplatin and 5-fluorouracil (CF) versus cisplatin (C) in recurrent or metastatic squamous cell carcinoma of the head and neck. A phase III study of the EORTC Head and Neck Cancer Cooperative Group. Ann Oncol 1994; 5:521] and [Forastiere A. A., Metch B., Schuller D. E. et al. Randomized comparison of cisplatin plus fluorouracil and carboplatin plus 5-fluorouracil versus methotrexate in advanced squamous-cell carcinoma of the head and neck: a Southwest Oncology Group study. J Clin Oncol 1992; 10:1245].

But it is among the gastrointestinal tumours where the 5-FU based regimens have the widest use. Colorectal cancer (CRC) is the third most common cancer in men (10% of the total) and the second in women (9.2%), with over 1.3 Million cases (746 000 men and 614 000 women) reported worldwide during 2012. The geographic incidence of CRC varies widely across the world, and the geographical patterns are very similar in men and women. Incidence rates vary ten-fold in both sexes worldwide, the highest estimated rates being in Australia/New Zealand (ASR 44.8 and 32.2 per 100,000 in men and women respectively), and the lowest in Western Africa (4.5 and 3.8 per 100,000). The incidence increases with age and is highest amongst the elder population, i.e. 60-64 years: 67.4; 65-69 years: 95.1; 70-74 years: 127.8; and ≥75 years: 196.2 per 100 000 [Ferlay J, Soerjomataram I, Ervik M, Dikshit R, Eser S, Mathers C, Rebelo M, Parkin D M, Forman D, Bray, F. GLOBOCAN 2012 v1.0, Cancer Incidence and Mortality Worldwide: IARC CancerBase No. 11. Lyon, France: International Agency for Research on Cancer; 2013].

Approximately 40-50% of the affected patients develop metastatic disease and more than half a million deaths are reported annually as a consequence of CRC [Jemal A, Bray F, Center M M, Ferlay J, Ward E, Forman D. Global cancer statistics. CA Cancer J Clin. 2011 March-April; 61(2):69-90]. Indeed CRC accounted for 694 000 deaths worldwide solely during 2012 (8.5% of the total) [Ferlay J, Soerjomataram I, Ervik M, Dikshit R, Eser S, Mathers C, Rebelo M, Parkin D M, Forman D, Bray, F. GLOBOCAN 2012 v1.0, Cancer Incidence and Mortality Worldwide: IARC Cancer-Base No. 11 [Internet]. Lyon, France: International Agency for Research on Cancer; 2013].

CRC patients are usually treated surgically and, in most circumstances, with curative intent. Surgery, in fact, remains the primary modality of treatment for malignancies of the lower gastrointestinal tract, and standard resection is the only therapy required for early-stage cancer [Nelson H, Petrelli N, Carlin A, Couture J, Fleshman J, Guillem J, et al. Guidelines 2000 for colon and rectal cancer surgery. J Natl Cancer Inst. 2001 Apr. 18; 93(8):583-96]. As the stage of the tumour advances, in terms of depth of penetration and lymph node involvement, the chance of cure with surgery alone diminishes and the rate of local recurrence increase. In such cases, surgery may either be combined with adjuvant treatment or be performed for palliative control of symptoms only.

Adjuvant therapies have been shown to improve treatment outcome in metastatic CRC with prolonged survival [Cunningham D, Atkin W, Lenz H J, Lynch H T, Minsky B, Nordlinger B, et al. Colorectal cancer. Lancet. 2010 Mar. 20; 375(9719):1030-47]. Standard first-line adjuvant therapy of CRC includes single and combination chemotherapy with the agent 5-Fluorouracil (5-FU) [Cunningham D (2010)]. Treatment with 5-FU is usually given in combination with high doses of folate (or Leucovorin, LV) which significantly enhances the therapeutic effect of 5-FU in metastatic colorectal carcinoma. In fact, modulation of 5-FU with LV in metastatic disease has shown prolongation of the time-to-progression (TTP) of disease [Petrelli N, Douglass H O Jr, Herrera L, Russell D, Stablein D M, Bruckner H W, et al. The modulation of fluorouracil with leucovorin in metastatic colorectal carcinoma: a prospective randomized phase III trial. Gastrointestinal Tumor Study Group. J Clin Oncol. 1989 October; 7(10):1419-26].

For colorectal tumors, the original response rate for 5-FU given as a monotherapy was only around 10%. By adding Leucovorin (LV) the response rate was improved to 21% [Thirion P, Michiels S, Pignon J P, Buyse M, Braud A C, Carlson R W, O'Connell M, Sargent P, Piedbois P (2004) Modulation of fluorouracil by leucovorin in patients with advanced colorectal cancer: an updated meta-analysis. J Clin Oncol 22(18):3766-3775]. However, LV needs to be converted to the active metabolite [6R]-5,10-methylenetetrahydrofolate (methyleneTHF), which subsequently forms a ternary complex with deoxyuridine monophosphate (dUMP) and the target enzyme thymidylate synthase (TS) in a reaction where dUMP is converted to dTMP [Jarmula A, Cieplak P, Montfort W R (2005) 5,10-Methylene-5,6,7,8-tetrahydrofolate conformational transitions upon binding to thymidylate synthase: molecular mechanics and continuum solvent studies. J Comput Aided Mol Des 19(2):123-136]. This reaction is inhibited when the fluorinated metabolite of 5-FU, FdUMP, binds the complex instead of dUMP [Parker W B, Cheng Y C (1990) Metabolism and mechanism of action of 5-fluorouracil. Pharmacol Ther 48(3):381-395]. As such, LV does not have antitumoral effect, but enhances the effect of 5-FU by providing methyleneTHF in abundance, which stabilizes the ternary complex [Porcelli L, Assaraf Y G, Azzariti A, Paradiso A, Jansen G, Peters G J (2011) The impact of folate status on the efficacy of colorectal cancer treatment. Curr Drug Metab 12(10):975-984]. The inhibition impacts cells with a high proliferation rate most, such as tumor epithelial cells. This in turn leads to suppression of DNA synthesis in the cells, which may lead to cell death by apoptosis.

The required metabolic activation of LV into methyleneTHF is likely to lead to interindividual differences, which may be the reason the response rate for 5-FU given as a monotherapy was only improved to 21%.

A reduced folate, fotrexorin calcium (CoFactor®) ((dl)-5,10,-methylenepteroyl-monoglutamate calcium salt, or [6R,S]-5,10-methylene-THF Ca salt), also known as racemic methyleneTHF, has been suggested as an alternative to LV based on the assumption that direct administration of the reduced folate methyleneTHF in place of LV might offer significant advantages with respect to clinical activity. CoFactor® is a 1:1 mixture of the two diastereoisomers [Odin, E., Carlsson, G., Frösing, R., Gustavsson, B., Spears, C. P., Larsson, P. A., 1998. Chemical stability and human plasma pharmacokinetics of reduced folates. Cancer Invest. 16, 447-455]. As the [6R]-isomer is the directly active co-substrate of TS, it was anticipated that the administration of CoFactor®, instead of leucovorin, would be advantageous due to lower inter- and intrapatient variability regarding both clinical safety and efficacy.

Indeed, in a Phase II Trial in previously untreated metastatic colorectal cancer, the response rate for CoFactor® was found to be 35% [Saif, M. W, Merritt, J, Robbins J, Stewart J., Schupp, J, 2006. Phase III Multicenter Randomized Clinical Trial to Evaluate the Safety and Efficacy of CoFactor®/5-Fluorouracil/Bevacizumab Versus Leucovorin/5-Fluorouracil/Bevacizumab as Initial Treatment for Metastatic Colorectal Carcinoma Clinical Colorectal Cancer, Vol. 6, No. 3, 229-234, 2006], and in another phase I/II clinical trial it was demonstrated that CoFactor® combined with 5-FU showed clinical benefit in pancreas cancer, defined as stable disease or tumor response, in 40% of patients [Saif, M. W., Makrilia N., Syrigos K., 2010. CoFactor: Folate Requirement for Optimization of 5-Fluouracil Activity in Anticancer Chemotherapy. Journal of Oncology Vol. 1-5]. However, apart from presenting an unnecessary hepatic detoxification burden, the unnatural (6S)-isomer is a partial competitive inhibitor of the natural [6R]-isomer regarding its effect as co-substrate for TS [Leary, R. P., Gaumont, Y., Kisliuk, R. L., 1974. Effects of the diastereoisomers of methylenetetrahydrofolate on the reaction catalyzed by thymidylate synthetase. Biochem. Biophys. Res. Commun. 56, 484-488]. Furthermore, in a Phase IIb study CoFactor® in colorectal cancer was not demonstrated to be more efficacious than leucovorin as no significant differences between the study arms with regard to either efficacy or safety could be found, and a planned Phase III study colorectal cancer was discontinued before completion [Press release: ADVENTRX Provides Update on Cofactor Program. Nov. 2, 2007]. There thus remains a need for an improved folate-enhanced 5-FU treatment protocol.

DEFINITIONS

As used herein, the terms IV or i.v. shall both mean intravenous.

As used herein, the term DLT shall refer to dose-limiting toxicity. Dose Limiting Toxicity (DLT) is a medical occurrence that is assessed as at least possibly related to a pharmaceutical product (i.e. to one or more chemotherapeutic agents) and is severe enough to prevent further increase in dosage or strength of treatment agent, or to prevent continuation of treatment at any dosage level.

As used herein, the term ORR shall refer to the Objective Response Rate, ie. the proportion of patients with reduction in tumor burden of a predefined amount.

This shall be calculated as follows: ORR=Sum of partial responses plus complete responses as per RECIST 1.1 (a set of published rules that define when tumours in cancer patients progress during treatments, the responses being defined as:

Complete Response (CR):
Disappearance of all target lesions. Any pathological lymph nodes (whether target or non-target) must have reduction in short axis to <10 mm.
Partial Response (PR):
At least a 30% decrease in the sum of diameters of target lesions, taking as reference the baseline sum diameters.
Progressive Disease (PD):
At least a 20% increase in the sum of diameters of target lesions, taking as reference the smallest sum on study (this includes the baseline sum if that is the smallest on study).
In addition to the relative increase of 20%, the sum must also demonstrate an absolute increase of at least 5 mm. (Note: the appearance of one or more new lesions is also considered progression).
Stable Disease (SD):
Neither sufficient shrinkage to qualify for PR nor sufficient increase to qualify for PD, taking as reference the smallest sum diameters while on study.
(Eisenhauer E A, Therasse P, Bogaerts J, Schwartz L H, Sargent D, Ford R, et al. New response evaluation criteria in solid tumours: revised RECIST guideline (version 1.1). Eur J Cancer. 2009 January; 45(2):228-47)

As used herein, the term dU shall refer to deoxyuridine.
As used herein, the term BSA refers to Body Surface Area
As used herein, the term proliferative diseases shall refer to a unifying concept that excessive proliferation of cells and turnover of cellular matrix contribute significantly to the pathogenesis of several diseases, including cancer, atherosclerosis, rheumatoid arthritis, psoriasis, idiopathic pulmonary fibrosis, scleroderma, cirrhosis of the liver, Crohn's disease and ulcerative colitis.

STATEMENTS OF INVENTION

Recently a stable formulation of [6R]-5,10-methylenetetrahydrofolate ([6R]-5,10-MTHF) has been developed which is a stable formulation of the naturally occurring diastereoisomer of MTHF. As mentioned earlier, [6R]-MTHF is also a metabolite of Leucovorin (LV). Unlike LV, [6R]-MTHF, does not need to undergo further metabolism, and may be directly involved in the formation of the FdUMP-TS ternary complex.

According to the present invention, it has surprisingly been found that by treating colorectal cancer patients according to a variety of chemotherapeutic protocols involving initial administration of 5-FU followed by administration of [6R]-MTHF, ORRs (objective response rates) of 50-60% can be achieved, and app. 65% of the treated patients experienced at least a 25% decrease in the sum of the diameters of target lesions, taking as reference the baseline sum diameters. It has further been demonstrated that [6R]-MTHF combined with 5-FU showed clinical benefit in colorectal cancer, defined as stable disease or tumor response, in >90% of treated patients.

Accordingly, in a first aspect of the invention, [6R]-5,10-methylene-tetrahydrofolate is provided for use in a human in the treatment of solid tumors such as cancer, which treatment comprises the following steps:
a) on Day 1, administering an IV bolus containing 10-1000 mg/m² (of BSA) 5-FU (or an analog or prodrug thereof), followed, either simultaneously or after a period of 10 min-4 hours, by
b) administering one or more IV boluses, each containing 5-1000 mg/m² [6R]-5,10-methylenetetrahydrofolate, followed by
c) administering a continuous infusion of 5-FU (or an analog or prodrug thereof) over a period of 46 hours, or until the end of Day 2, followed by
d) optionally administering one IV bolus containing 5-1000 mg/m2 (of BSA) [6R]-5,10-methylene-tetrahydrofolate before the end of Day 1, followed by
e) on Day 2, optionally administering one or more IV boluses each containing 5-1000 mg/m2 (of BSA) [6R]-5,10-methylene-tetrahydrofolate,
wherein step b) is optionally repeated up to 4 times on Day 1 with an interval of 10 min-4 hours between each bolus being administered, and wherein step e) is optionally repeated up to 4 times on Day 2 with an interval of between 10 min-60 min between each bolus being administered, and wherein all steps a)-e) are optionally repeated every 2 weeks for up to eight (8) cycles, i.e. up to sixteen (16) weeks.

In a second aspect of the invention there is provided a method of treating a human diagnosed with a solid tumor such as cancer, which method comprises:
a) on Day 1, administering an IV bolus containing 10-1000 mg/m² (of BSA) 5-FU (or an analog or prodrug thereof), followed, either simultaneously or after a period of 10 min-4 hours, by
b) administering one or more IV boluses, each containing 5-1000 mg/m2 (of BSA) [6R]-5,10-methylenetetrahydrofolate, followed by
c) administering a continuous infusion of 5-FU (or an analog or prodrug thereof) over a period of 46 hours, or until the end of Day 2, followed by
d) optionally administering one IV bolus containing 5-1000 mg/m2 (of BSA) [6R]-5,10-methylene-tetrahydrofolate before the end of Day 1, followed by
e) on Day 2, optionally administering one or more IV boluses each containing 5-1000 mg/m2 (of BSA) [6R]-5,10-methylene-tetrahydrofolate,
wherein step b) is optionally repeated up to 4 times on Day 1 with an interval of 10 min-60 min between each bolus being administered, and wherein step e) is optionally repeated up to 4 times on Day 2 with an interval of between 10 min-60 min between each bolus being administered, and wherein all steps a)-e) are optionally repeated every 2 weeks for up to eight (8) cycles, i.e. up to sixteen (16) weeks.

In a third aspect of the invention, [6R]-5,10-methylene-tetrahydrofolate is provided for use in a human in the treatment of solid tumors such as cancer, which treatment comprises the following steps:
a) on Day 1, administering an IV bolus containing 10-1000 mg/m² (of BSA) 5-FU (or an analog or prodrug thereof), followed, either simultaneously or after a period of 10 min-4 hours, by b) administering one or more IV boluses, each containing 5-1000 mg/m2 [6R]-5,10-methylenetetrahydrofolate, followed by c) optionally administering one IV bolus containing 5-1000 mg/m2 (of BSA) [6R]-5,10-methylene-tetrahydrofolate before the end of Day 1, followed by d) On Day 2, administering an IV bolus containing 10-1000 mg/m2 (of BSA) 5-FU (or an analog or prodrug thereof), followed, either simultaneously or after a period of 10 min-4 hours, by e) optionally administering one or more IV boluses each containing 5-1000 mg/m2 (of BSA) [6R]-5,10-methylene-tetrahydrofolate, wherein step b) is optionally repeated up to 4 times on Day 1 with an interval of 10 min-60 min between each bolus being administered, and wherein step d) is optionally repeated up to 4 times on Day 2 with an interval of between 10 min-60 min between each bolus being administered, and wherein all steps a)-e) are optionally repeated every 2 weeks for up to eight (8) cycles, i.e. up to sixteen (16) weeks.

In a fourth aspect of the invention, there is provided a method of treating a human diagnosed with a solid tumor such as cancer, which method comprises:

a) on Day 1, administering an IV bolus containing 10-1000 mg/m2 (of BSA) 5-FU (or an analog or prodrug thereof), followed, either simultaneously or after a period of 10 min-4 hours, by b) administering one or more IV boluses, each containing 5-1000 mg/m2 [6R]-5,10-methylenetetrahydrofolate, followed by c) optionally administering one IV bolus containing 5-1000 mg/m2 (of BSA) [6R]-5,10-methylene-tetrahydrofolate before the end of Day 1, followed by d) On Day 2, administering an IV bolus containing 10-1000 mg/m2 (of BSA) 5-FU (or an analog or prodrug thereof), followed, either simultaneously or after a period of 10 min-4 hours, by e) optionally administering one or more IV boluses each containing 5-1000 mg/m2 (of BSA) [6R]-5,10-methylene-tetrahydrofolate, wherein step b) is optionally repeated up to 4 times on Day 1 with an interval of 10 min-60 min between each bolus being administered, and wherein step d) is optionally repeated up to 4 times on Day 2 with an interval of between 10 min-60 min between each bolus being administered, and wherein all steps a)-e) are optionally repeated every 2 weeks for up to eight (8) cycles, i.e. up to sixteen (16) weeks.

FIGURES

FIG. 1 (Wettergren Y, Taflin H, Odin E, Kodeda K, Derwinger K; Cancer Chemother Pharmacol (2015) 75:37-47) A simplified overview of the folate metabolism. Within the cells, [6R]-MTHF ([6R]-5,10-methyleneTHF) can be used directly as a methyl donor in the synthesis of dTMP from dUMP. The reaction is catalyzed by the enzyme thymidylate synthase (TS). Isovorin® (levo-leucovorin, 5-formylTHF), on the other hand, needs to be converted in two steps to methyleneTHF. Treatment with 5-FU inhibits the synthesis of dTMP through the formation of FdUMP, which binds TS. DHF: dihydrofolate, DHFR: dihydrofolate reductase, SHMT1: serine hydroxymethyltransferase 1, MTHFR: methylenetetrahydrofolate reductase, MTHFD: methylenetetrahydrofolate dehydrogenase, MTHFS: methenyltetrahydrofolate synthetase.

FIG. 2 Results from the ongoing ISO-CC-005 study: Response rates according to RECIST 1.1 in thirty (30) $1^{st}$, $2^{nd}$, $3^{rd}$ and $5^{th}$ line patients assessed after 8 weeks and 16 weeks' treatment.

FIG. 3 Excerpt from Adventrx press release published 1 Oct. 2007 showing results of a Phase IIB study comparing Leucovorin with CoFactor, ie. [6R,S]-5,10-methyleneTHF.

DETAILED DESCRIPTION OF THE INVENTION

5-Fluorouracil (5-FU) is possibly the most widely used anticancer drug in the world. It was discovered by Spears et al. (Spears et al., Cancer Res. 42:450-56 (1982)) that the therapeutic mechanism of 5-FU against murine colon cancer was complete inhibition of the DNA enzyme thymidylate synthase (TS) or abrogation of TS activity. As mentioned hereinabove, folates (specifically, tetrahydrofolates) serve as one-carbon donors in the synthesis of purines and the pyrimidine deoxythymidine monophosphate (dTMP) and can be used to modulate the action of 5-FU; see also FIG. 1.

Several 5-FU based cancer treatment regimes have been developed where "folates" are given concomitantly or by other means as part of the treatment. Most of these regimes are variations over the FOLFOX regime which is the name of a combination chemotherapy treatment. It is also known as "Oxaliplatin de Gramont" or OxMdG, which means Oxaliplatin modified de Gramont. It is made up of the drugs:

FOL—Folinic acid (typically leucovorin or calcium folinate)

F—Fluorouracil (5-FU)

OX—Oxaliplatin

Examples of frequently administered chemotherapeutic agents within first- and second line metastatic CRC include 5-FU/folate, Capecitabine, Irinotecan, Oxaliplatin, Bevacizumab, Cetuximab, and Panitumamab, used alone or in combinations, e.g. FOLFOX (i.e. LV/5-FU/oxaliplatin), FOLFIRI (i.e. LV/5-FU/Irinotecan), FOLFOX/bevacizumab, and 5-FU-LV/bevacizumab and/or irinotecan.

As a specific example can be mentioned the FOLFOX4 protocol, whereby 200 mg/m$^2$ Leucovorin is administered iv over 2 hrs before 5-FU on day 1 and day 2 (5-FU 400 mg/m$^2$ iv bolus and then 600 mg/m$^2$ iv continuous infusion over 22 hrs, day 1 and day 2. The protocol includes the administration of Oxaliplatin (Eloxatin) 85 mg/m$^2$ iv day 1, and the treatment is given Q2w×12 cycles (see Goldberg R M et al. Pooled analysis of safety and efficacy of oxaliplatin plus 5-fluorouracil/leucovorin administrated bimonthly in elderly patients with colorectal cancer. J Clin Oncol 2006; 24:4085).

As another example can be mentioned the FOLFOX6 protocol whereby 400 mg/m$^2$ Leucovorin is administered iv over 2 hrs before 5-FU on day 1 followed by 2400 mg/m$^2$ iv over 46 hrs. The protocol includes the administration of Oxaliplatin (Eloxatin) 100 mg/m$^2$ iv over 2 hours on day 1, and the treatment is given Q2w×12 cycles (see Tournigand, C et al. FOLFIRI followed by FOLFOX6 or the reverse sequence in advanced colorectal cancer: A randomized GERCOR study. J Clin Oncol 2004; 22:229.

As another example can be mentioned the ROSWELL PARK REGIMEN whereby 5-FU is given as a 500 mg/m$^2$ BSA iv bolus 1 hour after starting the administration of a continuous infusion of leucovorin (500 mg/m$^2$ iv) over 2 hrs. This treatment is given Qw×6 wks (once per week for six weeks) every 8 weeks for 3-4 cycles (see Lembersky B C et al. Oral uracil and tegafur plus leucovorin compared with iv 5-FU and leucovorin in stage II and III carcinoma of the colon: results from national surgical adjuvant breast and bowel project protocol C-06. J Clin Oncol 2006; 24:2059).

As yet another example can be mentioned the study design for the planned CoFactor® Phase III study (Saif 2006, above), whereby CoFactor® was to be administered at a dose of 60 mg/m² over 2-3 minutes by I.V. bolus followed 20 minutes later by the administration of 5-FU as a bolus over 2-3 minutes at a dose of 500 mg/m² each week for 6 weeks, repeated every 8 weeks. In this study, oxaliplatin was replaced by bevacizumab to be administered at a dose of 5 mg/kg as a continuous I.V. over 90 minutes every 2 weeks.

Typically, in currently employed treatment protocols such as the ones cited hereinabove, 5-FU is always administered after the folate adjuvant (eg Leucovorin), whereas by the present invention treatment is initiated by administering a bolus of 5-FU. As stated hereinabove, the highest response rates (ORRs) achieved employing such protocols have been on the order of 35-40%.

According to the present invention, it was therefore surprisingly found that ORRs (response rates) of 50-60% can be achieved by treating colorectal cancer patients according to a regime whereby initial administration of 5-FU is followed by multiple IV boluses of [6R]-MTHF interspaced by an interval of about 10 min-4 hours between each bolus.

Accordingly, in a first aspect of the invention, [6R]-5,10-methylene-tetrahydrofolate is provided for use in the treatment in a human of a solid tumor such as cancer, which treatment comprises the following steps:
  a) on Day 1, administering an IV bolus containing 10-1000 mg/m² (of BSA) 5-FU (or an analog or prodrug thereof), followed, either simultaneously or after a period of 10 min-4 hours, by
  b) administering one or more IV boluses, each containing 5-1000 mg/m2 [6R]-5,10-methylenetetrahydrofolate, followed by
  c) administering a continuous infusion of 5-FU (or an analog or prodrug thereof) over a period of 46 hours, or until the end of Day 2, followed by
  d) optionally administering one IV bolus containing 5-1000 mg/m2 (of BSA) [6R]-5,10-methylene-tetrahydrofolate before the end of Day 1, followed by
  e) on Day 2, optionally administering one or more IV boluses each containing 5-1000 mg/m2 (of BSA) [6R]-5,10-methylene-tetrahydrofolate,
wherein step b) is optionally repeated up to 4 times on Day 1 with an interval of 10 min-60 min between each bolus being administered, and wherein step e) is optionally repeated up to 4 times on Day 2 with an interval of between 10 min-60 min between each bolus being administered, and wherein all steps a)-e) are optionally repeated every 2 weeks for up to eight (8) cycles, i.e. up to sixteen (16) weeks.

In an embodiment of the first aspect of the invention, step a) is preceded by administering an anticancer drug on Day 1, either as an IV bolus or as an infusion over a period of 1-4 hours.

In another embodiment [6R]-5,10-methylene-tetrahydrofolate is provided for the treatment according to the first aspect of the invention, wherein step a) is preceded by administering an anticancer drug on Day 1, either as an IV bolus or as an infusion over a period of 1-4 hours.

In a second aspect of the invention there is provided a method of treating a human diagnosed with a solid tumor such as cancer, which method comprises:
  a) on Day 1, administering an IV bolus containing 10-1000 mg/m² (of BSA) 5-FU (or an analog or prodrug thereof), followed, either simultaneously or after a period of 10 min-4 hours, by
  b) administering one or more IV boluses, each containing 5-1000 mg/m2 (of BSA) [6R]-5,10-methylenetetrahydrofolate, followed by
  c) administering a continuous infusion of 5-FU (or an analog or prodrug thereof) over a period of 46 hours, or until the end of Day 2, followed by
  d) optionally administering one IV bolus containing 5-1000 mg/m2 (of BSA) [6R]-5,10-methylene-tetrahydrofolate before the end of Day 1, followed by
  e) on Day 2, optionally administering one or more IV boluses each containing 5-1000 mg/m2 (of BSA) [6R]-5,10-methylene-tetrahydrofolate,
wherein step b) is optionally repeated up to 4 times on Day 1 with an interval of 10 min-60 min between each bolus being administered, and wherein step e) is optionally repeated up to 4 times on Day 2 with an interval of between 10 min-60 min between each bolus being administered, and wherein all steps a)-e) are optionally repeated every 2 weeks for up to eight (8) cycles, i.e. up to sixteen (16) weeks.

In a third aspect of the invention, [6R]-5,10-methylene-tetrahydrofolate is provided for use in the treatment in a human of a solid tumor such as cancer, which treatment comprises the following steps:
  a) on Day 1, administering an IV bolus containing 10-1000 mg/m² (of BSA) 5-FU (or an analog or prodrug thereof), followed, either simultaneously or after a period of 10 min-4 hours, by
  b) administering one or more IV boluses, each containing 5-1000 mg/m2 [6R]-5,10-methylenetetrahydrofolate, followed by
  c) optionally administering one IV bolus containing 5-1000 mg/m2 (of BSA) [6R]-5,10-methylene-tetrahydrofolate before the end of Day 1, followed by
  d) on Day 2, administering an IV bolus containing 10-1000 mg/m2 (of BSA) 5-FU (or an analog or prodrug thereof), followed, either simultaneously or after a period of 10 min-4 hours, by
  e) optionally administering one or more IV boluses each containing 5-1000 mg/m2 (of BSA) [6R]-5,10-methylene-tetrahydrofolate,
wherein step b) is optionally repeated up to 4 times on Day 1 with an interval of 10 min-60 min between each bolus being administered, and wherein step d) is optionally repeated up to 4 times on Day 2 with an interval of between 10 min-60 min between each bolus being administered, and wherein all steps a)-e) are optionally repeated every 2 weeks for up to eight (8) cycles, i.e. up to sixteen (16) weeks.

In another embodiment, in the treatment according to the third aspect of the invention, step a) is preceded by administering an anticancer drug on Day 1, either as an IV bolus or as an infusion over a period of 1-4 hours.

In a fourth aspect of the invention, there is provided a method of treating a human diagnosed with a solid tumor such as cancer, which method comprises:
  a) on Day 1, administering an IV bolus containing 10-1000 mg/m² (of BSA) 5-FU (or an analog or prodrug thereof), followed, either simultaneously or after a period of 10 min-4 hours, by
  b) administering one or more IV boluses, each containing 5-1000 mg/m² [6R]-5,10-methylenetetrahydrofolate, followed by
  c) optionally administering one IV bolus containing 5-1000 mg/m2 (of BSA) [6R]-5,10-methylene-tetrahydrofolate before the end of Day 1, followed by d) on Day 2, administering an IV bolus containing 10-1000 mg/m2 (of BSA) 5-FU (or an analog or prodrug thereof), followed, either simultaneously or after a period of 10 min-4 hours, by e) optionally administering one or more IV boluses each containing 5-1000 mg/m2 (of BSA) [6R]-5,10-methylene-tetrahydrofolate, wherein step b) is optionally repeated up to 4 times on Day 1 with an interval of 10 min 60 min between each bolus being administered, and wherein step d) is optionally repeated up to 4 times on Day 2 with an interval of between 10 min-60 min between each bolus being administered, and wherein all steps a)-e) are optionally repeated every 2 weeks for up to eight (8) cycles, i.e. up to sixteen (16) weeks.

During a currently (December 2017) ongoing clinical study it has also surprisingly been discovered that administration of [6R]-MTHF and 5-FU according to the first, second, third or fourth aspect of the present invention over a treatment period of at least 8 weeks lead to a prevention or retarding of the progression in a human of solid tumors. No statistically significant progression of said solid tumors was observed between 8 and 16 weeks after initializing treatment.

In a fifth aspect of the invention, [6R]-5,10-methylene-tetrahydrofolate is therefore provided for use in the prevention or retarding of the progression in a human of solid tumors, including cancer, which comprises performing and repeating steps a) to e) according to the first aspect of the present invention, over a total treatment period of at least 8 weeks.

In a preferred embodiment of the fifth aspect, there is provided [6R]-5,10-methylene-tetrahydrofolate for use in the prevention or retarding of the progression in a human of solid tumors, whereby steps a) to e) according to the first aspect of the present invention are performed and repeated over a total treatment period of at least 16 weeks, and whereby no statistically significant progression of said solid tumors is observed between 8 and 16 weeks after initializing treatment.

In a sixth aspect of the invention, there is provided a method for preventing or retarding the progression in a human diagnosed with a solid tumor such as cancer, which comprises performing and repeating steps a) to e) according to the second aspect of the present invention, over a total treatment period of at least 8 weeks.

In a preferred embodiment of the sixth aspect, there is provided a method for preventing or retarding the progression in a human diagnosed with a solid tumor such as cancer, which comprises performing and repeating steps a) to e) according to the second aspect of the present invention, over a total treatment period of at least 8 weeks whereby no statistically significant progression of said solid tumors is observed between 8 and 16 weeks after initializing treatment.

In a specific embodiment of the invention there is provided [6R]-5,10-methylene-tetrahydrofolate for use in the treatment in a human of solid tumors, including cancer, which treatment comprises the following steps:

a) on Day 1, providing an IV bolus for administration of 400 mg/m² (of BSA) 5-FU (or an analog or prodrug thereof), followed, after a period of 30 min, by b) providing an IV bolus for administration of 30 mg/m2 [6R]-5,10-methylene-tetrahydrofolate, followed by c) providing an IV solution for continuous infusion of 5-FU (or an analog or prodrug thereof) over a period of 46 hours, or until the end of Day 2, followed by d) on Day 2, providing two IV boluses, interspaced by a period of 30 minutes, each for administration of 30 mg/m2 [6R]-5,10-methylenetetrahydrofolate, wherein all steps a)-d) are repeated every second week for up to eight (8) cycles, i.e. up to sixteen (16) weeks.

In a preferred embodiment of the invention there is provided [6R]-5,10-methylene-tetrahydrofolate for use in the treatment in a human of solid tumors, including cancer, which treatment comprises the following steps:

a) on Day 1, providing an IV bolus for administration of 400 mg/m² (of BSA) 5-FU (or an analog or prodrug thereof), followed, after a period of 30 min, by b) providing an IV bolus for administration of 60 mg/m² [6R]-5,10-methylene-tetrahydrofolate, followed by c) providing an IV solution for continuous infusion of 5-FU (or an analog or prodrug thereof) over a period of 46 hours, or until the end of Day 2, followed by d) on Day 2, providing two IV boluses, interspaced by a period of 30 minutes, each for administration of 60 mg/m² [6R]-5,10-methylenetetrahydrofolate, wherein all steps a)-d) are repeated every second week for up to eight (8) cycles, i.e. up to sixteen (16) weeks.

In another specific embodiment of the invention there is provided [6R]-5,10-methylene-tetrahydrofolate for use in the treatment in a human of solid tumors, including cancer, which treatment comprises the following steps:

a) on Day 1, providing an IV bolus for administration of 400 mg/m² (of BSA) 5-FU (or an analog or prodrug thereof), followed, after a period of 30 min, by b) providing an IV bolus for administration of 120 mg/m² [6R]-5,10-methylene-tetrahydrofolate, followed by c) providing an IV solution for continuous infusion of 5-FU (or an analog or prodrug thereof) over a period of 46 hours, or until the end of Day 2, followed by d) on Day 2, providing two IV boluses, interspaced by a period of 30 minutes, each for administration of 120 mg/m² [6R]-5,10-methylenetetrahydrofolate, wherein all steps a)-d) are repeated every second week for up to eight (8) cycles, i.e. up to sixteen (16) weeks.

In a specific embodiment of the invention there is provided [6R]-5,10-methylene-tetrahydrofolate for use in the treatment in a human of solid tumors, including cancer, which treatment comprises the following steps:

a) on Day 1, providing an IV bolus for administration of 400 mg/m² (of BSA) 5-FU (or an analog or prodrug thereof), followed, after a period of 30 min, by b) providing an IV bolus for administration of 30 mg/m² [6R]-5,10-methylene-tetrahydrofolate, followed by c) providing an IV solution for continuous infusion of 5-FU (or an analog or prodrug thereof) over a period of 46 hours, or until the end of Day 2, followed by wherein all steps a)-c) are repeated every second week for up to eight (8) cycles, i.e. up to sixteen (16) weeks.

In a preferred embodiment of the invention there is provided [6R]-5,10-methylene-tetrahydrofolate for use in the treatment in a human of solid tumors, including cancer, which treatment comprises the following steps:

a) on Day 1, providing an IV bolus for administration of 400 mg/m² (of BSA) 5-FU (or an analog or prodrug thereof), followed, after a period of 30 min, by b) providing an IV bolus for administration of 60 mg/m² [6R]-5,10-methylene-tetrahydrofolate, followed by c) providing an IV solution for continuous infusion of 5-FU (or an analog or prodrug thereof) over a period of 46 hours, or until the end of Day 2, followed by wherein all steps a)-c) are repeated every second week for up to eight (8) cycles, i.e. up to sixteen (16) weeks.

In another specific embodiment of the invention there is provided [6R]-5,10-methylene-tetrahydrofolate for use in the treatment in a human of solid tumors, including cancer, which treatment comprises the following steps:
- a) on Day 1, providing an IV bolus for administration of 400 mg/m² (of BSA) 5-FU (or an analog or prodrug thereof), followed, after a period of 30 min, by
- b) providing an IV bolus for administration of 120 mg/m² [6R]-5,10-methylene-tetrahydrofolate, followed by
- c) providing an IV solution for continuous infusion of 5-FU (or an analog or prodrug thereof) over a period of 46 hours, or until the end of Day 2, followed by wherein all steps a)-d) are repeated every second week for up to eight (8) cycles, i.e. up to sixteen (16) weeks.

In another embodiment there is provided the use of [6R]-5,10-methylene-tetrahydrofolate in the preparation of a medicament for reducing the toxicity and/or improving the therapeutic effect of 5-fluorouracil (5-FU), wherein said medicament is to be co-administered with 5-fluorouracil (5-FU) for the treatment of solid tumors such as cancer, according to the following regimen:
- a) on Day 1, administering an IV bolus containing 10-1000 mg/m2 (of BSA) 5-FU (or an analog or prodrug thereof), followed, either simultaneously or after a period of 10 min-4 hours, by
- b) administering one or more IV boluses, each containing 5-1000 mg/m2 [6R]-5,10-methylenetetrahydrofolate interspaced by a period of 10-60 minutes, followed by
- c) administering a continuous infusion of 5-FU (or an analog or prodrug thereof) over a period of 46 hours, or until the end of Day 2, followed by
- d) optionally administering one IV bolus containing 5-1000 mg/m2 (of BSA) [6R]-5,10-methylene-tetrahydrofolate before the end of Day 1, followed by
- e) on Day 2, optionally administering one or more IV boluses each containing 5-1000 mg/m2 (of BSA) [6R]-5,10-methylene-tetrahydrofolate, wherein step b) is optionally repeated up to 4 times on Day 1 with an interval of 10 min-4 hours between each repetition, and wherein step e) is optionally repeated up to 4 times on Day 2 with an interval of between 10 min-60 minutes between each bolus being administered, and wherein all steps a)-e) are optionally repeated every 2 weeks for up to eight (8) cycles, i.e. up to sixteen (16) weeks.

In another specific embodiment of the invention there is provided a pharmaceutical composition for treating solid tumors such as cancer comprising [6R]-5,10-methylene-tetrahydrofolate, wherein said composition is co-administrated with 5-fluorouracil (5-FU) by the following dosage regimen:
- a) on Day 1, administering an IV bolus containing 10-1000 mg/m2 (of BSA) 5-FU (or an analog or prodrug thereof), followed, either simultaneously or after a period of 10 min-4 hours, by
- b) administering one or more IV boluses, each containing 5-1000 mg/m2 [6R]-5,10-methylenetetrahydrofolate interspaced by a period of 10-60 minutes, followed by
- c) administering a continuous infusion of 5-FU (or an analog or prodrug thereof) over a period of 46 hours, or until the end of Day 2, followed by
- d) optionally administering one IV bolus containing 5-1000 mg/m2 (of BSA) [6R]-5,10-methylene-tetrahydrofolate before the end of Day 1, followed by
- e) on Day 2, optionally administering one or more IV boluses each containing 5-1000 mg/m2 (of BSA) [6R]-5,10-methylene-tetrahydrofolate, wherein step b) is optionally repeated up to 4 times on Day 1 with an interval of 10 min-4 hours between each repetition, and wherein step e) is optionally repeated up to 4 times on Day 2 with an interval of between 10 min-60 minutes between each bolus being administered, and wherein all steps a)-e) are optionally repeated every 2 weeks for up to eight (8) cycles, i.e. up to sixteen (16) weeks.

In yet another specific embodiment of the invention there is provided a pharmaceutical composition for treating solid tumors such as cancer comprising 5-fluorouracil (5-FU), wherein said composition is administrated with [6R]-5,10-methylene-tetrahydrofolate by the following dosage regimen:
- a) on Day 1, administering an IV bolus containing 10-1000 mg/m2 (of BSA) 5-FU (or an analog or prodrug thereof), followed, either simultaneously or after a period of 10 min-4 hours, by
- b) administering one or more IV boluses, each containing 5-1000 mg/m2 [6R]-5,10-methylenetetrahydrofolate interspaced by a period of 10-60 minutes, followed by
- c) administering a continuous infusion of 5-FU (or an analog or prodrug thereof) over a period of 46 hours, or until the end of Day 2, followed by
- d) optionally administering one IV bolus containing 5-1000 mg/m2 (of BSA) [6R]-5,10-methylene-tetrahydrofolate before the end of Day 1, followed by
- e) on Day 2, optionally administering one or more IV boluses each containing 5-1000 mg/m2 (of BSA) [6R]-5,10-methylene-tetrahydrofolate, wherein step b) is optionally repeated up to 4 times on Day 1 with an interval of 10 min-4 hours between each repetition, and wherein step e) is optionally repeated up to 4 times on Day 2 with an interval of between 10 min-60 minutes between each bolus being administered, and wherein all steps a)-e) are optionally repeated every 2 weeks for up to eight (8) cycles, i.e. up to sixteen (16) weeks.

In another specific embodiment there is provided the use of [6R]-5,10-methylene-tetrahydrofolate in the manufacture of a medicament for the treatment of solid tumors such as cancer wherein the medicament is to be co-administrated with 5-fluorouracil (5-FU) according to the following regimen:
- a) on Day 1, administering an IV bolus containing 10-1000 mg/m2 (of BSA) 5-FU (or an analog or prodrug thereof), followed, either simultaneously or after a period of 10 min-4 hours, by
- b) administering one or more IV boluses, each containing 5-1000 mg/m2 [6R]-5,10-methylenetetrahydrofolate interspaced by a period of 10-60 minutes, followed by
- c) administering a continuous infusion of 5-FU (or an analog or prodrug thereof) over a period of 46 hours, or until the end of Day 2, followed by
- d) optionally administering one IV bolus containing 5-1000 mg/m2 (of BSA) [6R]-5,10-methylene-tetrahydrofolate before the end of Day 1, followed by
- e) on Day 2, optionally administering one or more IV boluses each containing 5-1000 mg/m2 (of BSA) [6R]-5,10-methylene-tetrahydrofolate, wherein step b) is optionally repeated up to 4 times on Day 1 with an interval of 10 min-4 hours between each repetition, and wherein step e) is optionally repeated up to 4 times on Day 2 with an interval of between 10 min-60 minutes between each bolus being administered, and wherein all steps a)-e) are optionally repeated every 2 weeks for up to eight (8) cycles, i.e. up to sixteen (16) weeks.

In preferred embodiments of any aspect of the current invention, an IV bolus [6R]-5,10-methylenetetrahydrofolate contains 30, 60 or 120 mg/m² (of BSA) [6R]-5,10-methylene-tetrahydrofolate.

In another preferred embodiment of any of the aspects of the invention, [6R]-5,10-methylenetetrahydrofolate is administered twice on Day 1, and no administration on Day 2.

In another embodiment of any of the aspects of the invention, step a) is preceded by administering one or more anticancer drugs on Day 1, either as an IV bolus or as an infusion over a period of 1-4 hours. In separate embodiments the anticancer drug may be one or more drugs selected from Platinum Drugs such as cisplatin (CDDP), carboplatin (CBDCA) and oxaliplatin (oloxetin), Antimetabolites such as 5-fluoruracil (5-FU), capecetabine (Xeloda), gemcitabine (Gemzar), methotrexate and pemetrexed (Alimta), Antitumor antibiotics, such as doxorubicin (Adriamycin), daunorubicin, actinomycin-D and mitomycin-C (MTC), Topoisomerase Inhibitors, such as irinotecan (CPT-11), topotecan (hycamtin) and etoposide (VP-16), Mitotic Inhibitors, such as paclitaxel (Taxol), docetaxel (Taxotere) and vincristine (Oncovin), Corticosteroids, such as prednisone, methylprednisolone (Solumedrol) and dexamethasone (Decadron), or may be selected from Targeted Therapies including Monoclonal Antibodies (MABs), such as cetuximab (Erbitux), rituximab (Rituxan) and bevacizumab (Avastin), or Small Molecular EGFR Inhibitors, such as gefitinib (Iressa), or may be selected from Hormone Therapies, such as tamoxifen (Nolvadex) and bicalutamide (Casodex), or may be selected from Cancer Immunotherapy Agents, including Monoclonal Antibodies, or Immune Check Point Inhibitors, such as PD-1 inhibitors including pembrolizumab (Keytruda) and nivolumab (Opdivo), or PD-L1 Inhibitors including atezolizumab (Tecentriq), or Cancer Vaccines.

In another embodiment of any of the aspects of the invention, the administered [6R]-5,10-methylene-tetrahydrofolate is a single diastereomer with a diastereomeric excess (d.e.) of >90% d.e., such as >93% d.e., such as >95% d.e., such as >98% d.e., such as >99% d.e., such as >99.5% d.e. or such as >99.9% d.e. In a preferred embodiment the administered [6R]-5,10-methylene-tetrahydrofolate is a single diastereomer with a diastereomeric excess (d.e.) of >98% d.e.

In another embodiment of any of the aspects the invention, the solid tumor is selected from various cancer forms including colon cancer, stomach cancer, breast cancer, bowel cancer, gallbladder cancer, lung cancer (specifically adenocarcinoma), colorectal cancer (CRC) including metastatic CRC, head and neck cancer, liver cancer, osteosarcoma and pancreatic cancer.

In a particular embodiment of any of the aspects the invention the solid tumor is selected from colon cancer and colorectal cancer.

In another embodiment of the invention, the 5-FU analog or prodrug is selected from fluorinated pyrimidine bases such as capecitabine (Xeloda), ie. N4-pentyloxycarbonyl-5'-deoxy-5-fluorocytidine, tegafur, 5-fluoro-pyrimidinone, UFT, doxifluridine, 2'-deoxy-5 fluorouridine, 5'-deoxy-5-fluorouridine, 1-(2'-oxopropyl)-5-FU, and alkyl-carbonyl-5-FU, BOF-A2, ftorafur (TS-1), and S-1.

In an embodiment [6R]-5,10-methylenetetrahydrofolate ([6R]-MTHF) is employed as a solid form which is soluble in water, such as a lyophilisate or a salt, optionally stabilized by one or more suitable excipients and/or antioxidants such as citric acid or ascorbic acid or salt forms thereof.

In an embodiment [6R]-5,10-methylenetetrahydrofolate ([6R]-MTHF) is administered as one or more IV boluses, each bolus containing 5-1000 mg/m2 BSA, such as 5 mg/m2 BSA, such as 7 mg/m2 BSA, such as 10 mg/m2 BSA, such as 15 mg/m2 BSA, such as 30 mg/m2 BSA, such as 60 mg/m2 BSA, such as 120 mg/m2 BSA, such as 240 mg/m2 BSA, such as 480 mg/m2 BSA, such as 720 mg/m2 BSA or such as 960 mg/m2 BSA.

In a further embodiment [6R]-5,10-methylenetetrahydrofolate is administered up to 4 times on Day 1 with an interval of 20-30 min between each bolus being administered.

In a another embodiment [6R]-5,10-methylenetetrahydrofolate is administered up to 4 times on Day 2 with an interval of 20-30 min between each bolus being administered.

In yet a another embodiment [6R]-5,10-methylenetetrahydrofolate is administered up to 4 times both on Day 1 and on Day 2 with an interval of 20-30 min between each bolus being administered.

In an embodiment 5-fluorouracil (5-FU) is administered as one or more IV boluses, each bolus containing 10-1000 mg/m2 BSA, such as 300 mg/m2 BSA, such as 400 mg/m2 BSA, such as 500 mg/m2 BSA, such as 600 mg/m2 BSA, such as 700 mg/m2 BSA, such as 800 mg/m2 BSA, such as 900 mg/m2 BSA or such as 1000 mg/m2 BSA.

In an embodiment of any of the aspects of the invention, a treatment cycle comprises two days. This regimen may optionally be repeated every 2 weeks for four (4) cycles, i.e. a total of eight (8) weeks.

In another embodiment of any of the aspects of the invention, Day 1 and Day 2 of the treatment cycle are separated by a period of 1-5 days, for example for monitoring purposes.

In a preferred embodiment of any of the aspects of the invention, a treatment cycle comprises two days. This regimen may optionally be repeated every 2 weeks for eight (8) cycles, i.e. a total of sixteen (16) weeks.

In another embodiment of any of the aspects of the invention, the treatment cycle is extended beyond Day 1 and Day 2 by a period of 1-5 days.

EXAMPLES

The safety and efficacy of [6R]-5,10-methylenetetrahydrofolate ([6R]-MTHF) is analyzed in an open-label, multiple-site, Phase I/II Dose Cohort Trial (ISO-CC-005) in combination with a fixed dose of 5-Fluorouracil (5-FU) alone or together with a fixed dose of Bevacizumab, Oxaliplatin or Irinotecan in patients with stage IV colorectal cancer. A maximum of 63 Stage IV CRC patients eligible for $1^{st}$, $2^{nd}$ or $3^{rd}$ line treatment are planned to be enrolled in this study disposed as follows: three to six patients in each dose cohort, and three additional patients in one dose cohort in each treatment arm according to the following study design (Table 1).

TABLE 1

Initial Doses of the Chemotherapy Agents (Bevacizumab, Oxaliplatin, Irinotecan, and/or 5-FU) and of the Study Drug ([6R]-5,10-methylenetetrahydrofolate)

| Treatment Arm | Cohort* | Bevacizumab At approx. −180 minutes (infusion 30 to 90 min) | Oxaliplatin¶ At approx. −60 minutes (infusion 15 to 120 min) | Irinotecan# At approx. −60 minutes (infusion 30 to 90 min) | 5-FU§* At 0 minute (bolus) | [6R]-5,10-methylene-tetrahydro-folate At approx. 30 minutes (bolus)$^a$ | 5-FU At approx. 35 minutes (46-hour continuous infusion)$^a$ |
|---|---|---|---|---|---|---|---|
| Arm 1 | Cohort 1 | N/A | N/A | N/A | 500 mg/m² | 30 mg/m² | N/A |
|  | Cohort 2 | N/A | N/A | N/A | 500 mg/m² | 60 mg/m² | N/A |
|  | Cohort 8 | N/A | N/A | N/A | 500 mg/m² | 120 mg/m² | N/A |
|  | Cohort 9 | N/A | N/A | N/A | 500 mg/m² | 240 mg/m² | N/A |
| Arm 2 | Cohort 4 | N/A | 85 mg/m² | N/A | 500 mg/m² | 30 mg/m² | N/A |
|  | Cohort 5 | N/A | 85 mg/m² | N/A | 500 mg/m² | 60 mg/m² | N/A |
| Arm 3 | Cohort 6 | N/A | N/A | 180 mg/m² | 500 mg/m² | 30 mg/m² | N/A |
|  | Cohort 7 | N/A | N/A | 180 mg/m² | 500 mg/m² | 60 mg/m² | N/A |
| Arm 4 | Cohort 12 | N/A | 85 mg/m² | N/A | 400 mg/m² | 60 mg/m²$^{2a}$ | 2 400 mg/m² |
|  | Cohort 13 | N/A | 85 mg/m² | N/A | 400 mg/m² | 120 mg/m²$^{2a}$ | 2 400 mg/m² |
|  | Cohort 14 | N/A | 85 mg/m² | N/A | 400 mg/m² | 240 mg/m²$^{2a}$ | 2 400 mg/m² |
| Arm 5 | Cohort 15 | 5 mg/kg | 85 mg/m² | N/A | 400 mg/m² | SP2D$^{a,b}$ | 2 400 mg/m² |

Abbreviation:
N/A: not applicable,
SP2D: selected phase 2 dose.
¶The time-point window for Oxaliplatin administration will be expanded to allow infusion times of up to 120 minutes, if necessary
The time-point window for Irinotecan administration will be expanded to allow infusion times of up to 90 minutes, if necessary.
§The administered bolus 5-FU dose should not surpass the maximum recommended daily dose of 1000 mg, regardless of the body surface area.
*Cohort #3, Cohort #10 and Cohort #11, originally included in earlier versions of this clinical study protocol, have been erased.
$^a$In Treatment Arm #4 (Cohorts #12, #13, and #14) and Arm #5 (Cohort #15) the total dose of ([6R]-5,10-methylenetetrahydrofolate will be divided into two (2) i.v. bolus injections dispensed approximately 30 and 60 minutes after administration of 5-FU bolus injection (at 0 minute), respectively. The continuous 5-FU infusion will be paused for administration of the second injection of ([6R]-5,10-methylenetetrahydrofolate.
$^b$The dose level of ([6R]-5,10-methylenetetrahydrofolate in Treatment Arm #4 (MOFOX) assessed as the dose level with the most favourable profile for the following investigation.

[6R]-5,10-Methylenetetrahydrofolic acid is formulated as a lyophylised powder containing 100 mg per vial (calculated as free acid). Dosing: Rapid i.v. bolus injections at a fixed dose of 30, 60, 120 or 240 mg/m², will be administered approximately 30 minutes after administration of 5-FU on Day 1 and Day 2 in each treatment cycle in all dose cohorts of the study (i.e. regardless of treatment arm). The regimen will be repeated every second week for up to eight (8) cycles, i.e. up to sixteen (16) weeks.

5-FU (5-fluorouracil) is formulated as injection solution. Dosing: 5-FU will be administered as i.v. bolus injections on Day 1 and Day 2 in each treatment cycle. In Arm #2 and Arm #3 of the study, 5-FU will be administered approximately 60 minutes after start of Oxaliplatin or Irinotecan administration, respectively (see description below). The regimen will be repeated every second week for up to eight (8) cycles, i.e. up to sixteen (16) weeks.

Oxaliplatin is formulated as a concentrated infusion solution. Dosing: Oxaliplatin will be administered as i.v. infusion during 15-120 minutes on Day 1 in each treatment cycle in treatment Arm #2 of the study (i.e. Cohorts #4, #5, #10, and #11) and repeated every second week for up to eight (8) cycles, i.e. up to sixteen (16) weeks. Caution will be taken regarding toxicity associated with administration that may affect rate of infusion (e.g. grade ≤2 allergy, laryngopharyngeal dysesthesias, and laryngeal spasm). In such cases, rate of Oxaliplatin administration should be prolonged in following cycles according to clinical practice recommendations.

Irinotecan is formulated as a concentrated infusion solution. Dosing: Irinotecan will be administered as i.v. infusion during 30-90 minutes on Day 1 in each treatment cycle in treatment Arm #3 of the study (i.e. Cohorts #6 and #7) and repeated every second week for up to eight (8) cycles, i.e. up to sixteen (16) weeks. Caution will be taken regarding early toxicity (within 24 hours) associated with Irinotecan administration, i.e. acute cholinergic syndrome, characterized by early diarrhoea, emesis, diaphoresis, abdominal cramping, and, less commonly, hyperlacrimation and rhinorrhoea. In such cases, the use of anticholinergics according to clinical practice recommendations is necessary.

Avastin (Bevacizumab) is formulated as a concentrated infusion solution. Dosing: Bevacizumab is administered as i.v. infusion during 30-90 minutes on Day 1 in each treatment cycle in Treatment Arm #5 of the study (i.e. Cohorts #15) and repeated every second week for up to eight (8) cycles, i.e. up to sixteen (16) weeks.

Bevacizumab associated Toxicity: Based on data from clinical trials in which patients primarily were treated with Bevacizumab in combination with chemotherapy, the following may be recognized as Bevacizumab associated toxicity: Most common serious adverse events: gastrointestinal perforations, haemorrhage (including pulmonary haemorrhage/haemoptysis), and arterial thromboembolism; Most common adverse events: hypertension, fatigue or asthenia, diarrhoea, and abdominal pain.

Results

ISO-CC-005 is an open clinical phase I/II tolerability and dose definition study designed to evaluate safety and define the [6R]-MTHF dose for continued development. It evaluates four doses of [6R]-MTHF in combination with 5-FU with or without the different combinations of irinotecan or oxaliplatin and bevacizumab in patients with metastatic Colorectal Cancer using 4 different protocols:

MOD+5-FU: [6R]-MTHF in combination with 5-FU only, similar to Nordic FLV protocol MOD+FLIRI: [6R]-MTHF in combination with 5-FU and Irinotecan, similar to Nordic FLIRI protocol MOD+FLOX: [6R]-MTHF in combination with 5-FU and Oxaliplatin, similar to Nordic FLOX protocol MOFOX: [6R]-MTHF in combination with 5-FU and Oxaliplatin, similar to FOLFOX-6 protocol The patients belong to several treatment lines ranging from first to third and even fifth lines. The results of the study are regularly assessed, and the results from the group of patients undergoing $1^{st}$ line treatment and partially the group of patients undergoing $2^{nd}$, $3^{rd}$ and $5^{th}$ line treatment have previously (in August 2017) and again (December 2017) been analyzed. The clinical study is still ongoing.

In total 30 patients were initially analyzed after 8 weeks' treatment in August 2017, including both $1^{st}$, $2^{nd}$, $3^{rd}$ and $5^{th}$ line patients (see FIG. 2). Of these 30 patients, 4 (13%) showed progressive disease, 18 (60%) showed stable disease and 8 (27%) showed partial response. In terms of line of treatment, 100% of the patients undergoing $1^{st}$ line treatment showed clinical benefit in colorectal cancer, defined as stable disease or partial response, and for this group of patients the ORR was 50%.

By September 2017 the gastrointestinal (GI) adverse effects (AEs) for in total 37 ISO-CC-005 patients had been analyzed. Of the 37 patients, only 2 (two) patients (5.4%) reported a GI adverse event (defined as nausea, vomiting and/or dehydration) of grade 3 or greater.

By December 2017, a total or 25 patients from the ISO-CC-005 study receiving $2^{nd}$, $3^{rd}$ or $5^{th}$ line treatment had been analyzed for effect of 8 weeks' treatment, and eight (8) $1^{st}$ line patients also for 16 weeks' treatment (16 weeks is considered the standard schedule for cancer treatment according to clinical practice guidelines for ESMO (European Society for Medical Oncology)). (see FIG. 2). Four (4) $1^{st}$ line patients could not be followed for the additional 8 weeks' treatment due to study protocol formalities. No further $1^{st}$ line patients had been analysed at this point.

In line with the general expectations for cancer patients who have not responded well to $1^{st}$ line treatment, the $2^{nd}$, $3^{rd}$ or $5^{th}$ line treatment patients did not respond as well as the $1^{st}$ line patients. Nevertheless, no less than 64% of these patients showed clinical benefit in colorectal cancer, defined as stable disease or partial response (see FIG. 2) when analysed after 8 weeks' treatment, which is a surprisingly high percentage.

For the remaining eight (8) $1^{st}$ line patients who had received 16 weeks of treatment, no progression in the cancer was observed after the initial 8 weeks' treatment. Thus, the 3 patients showing Stable Disease at 8 weeks still showed Stable Disease at 16 weeks, and the 5 patients showing Partial Response at 8 weeks still showed Partial Response at 16 weeks. This corresponds to 100% of the $1^{st}$ line patients showing clinical benefit in colorectal cancer, and an ORR of 63%.

It should be noted that the 3 patients who had been treated according to the MOFOX protocol (two $1^{st}$ line and one $2^{nd}$ line) and showed Partial Response after 8 weeks' treatment still showed Partial Response after 8 weeks' treatment, and that the single 2nd-line treatment patient who was on MOFOX treatment was the only $2^{nd}$-line patient showing Partial Response after 16 weeks MOFOX treatment.

The very high ORRs (observed both at 8 and 16 weeks) and low incidence of Adverse Events (AEs) (analyzed at 8 weeks) are surprising, given the fact that CoFactor, which is the 1:1 diastereomer mixture [6R,S]-MTHF, was shown in a Phase IIb study comparing CoFactor with Leucovorin in first-line patients to lead to 7.7% CoFactor patients reporting at least one AE of grade 3 or greater vs 3.3% for Leucovorin, and further that the ORRs for CoFactor and Leucovorin were found to be 10.7% and 13.3% respectively (Adventrx Press Release 1 Oct. 2007, FIG. 3).

Without being bound by theory, the inventors speculate that the difference between CoFactor and [6R]-MTHF—as assessed by their difference in efficacy and AEs in comparative studies with Leucovorin—may be ascribed to the presence of 50% [6S]-MTHF in CoFactor, ie. the opposite diastereomer of [6R]-MTHF. As CoFactor was given up several years ago it is not possible to directly address this question in a clinical setting, but it is well known that for many pharmaceutically active compounds there can be a big difference in both desired effect and side effects when comparing pure enantiomers with racemates, or when comparing geometric isomers such as cis- and trans-isomers. In the present diastereomeric isomer situation, the unnatural [6S]-diastereomeric isomer the unnatural [6S]-isomer has thus already been demonstrated to be a partial competitive inhibitor of the natural [6R]-isomer [6R]-MTHF regarding its effect as co-substrate for Thymidylate Synthase [Leary, R. P., Gaumont, Y., Kisliuk, R. L., 1974. Effects of the diastereoisomers of methylenetetrahydrofolate on the reaction catalyzed by thymidylate synthetase. Biochem. Biophys. Res. Commun. 56, 484-488].

The study thus far has demonstrated that [6R]-MTHF combined with 5-FU shows clinical benefit in colorectal cancer, defined as stable disease or partial response:

in a very large proportion of treated patients, in a number of different treatment protocols, and for $1^{st}$, $2^{nd}$ $3^{rd}$ or $5^{th}$ line treatment.

In particular, the study has demonstrated that [6R]-MTHF combined with 5-FU provides very good results for the group of patients who have previously received other cancer therapies, and that treatment with [6R]-5,10-methylene-tetrahydrofolate in combination with 5-FU according to the present invention may prevent or retard the progression of solid tumors.

The study results further support that [6R]-MTHF in combination with different forms of cytostatic agents can be safe, and that [6R]-MTHF may be efficacious and safe for these severely ill patients. The Dose Limiting Toxicity (DLT) of the cytostatic agents employed in cancer treatment typically prevents further increase in dosage or strength of the treatment agent, or prevent continuation of treatment at a current dosage level. The DLT therefore often severely limits the doses of cytostatic agents which can be given to a patient. The results of the ISO-CC-005 study achieved so far indicate that the toxicity of 5-FU when combined with [6R]-MTHF is reduced, compared to combinations of 5-FU with other folate adjuvants. This may allow the use of higher doses of 5-FU without causing dose limiting side effects.

The invention claimed is:

1. A method of treating a human diagnosed with a solid tumor, including cancer, which method comprises:

a) on Day 1, administering an IV bolus containing 10-1000 mg/m$^2$ of body surface area (BSA) 5-fluorouracil (5-FU), or an analog or prodrug thereof, followed, either simultaneously or after a period of 10 min-4 hours, by b) administering one or more IV boluses, each containing 5-1000 mg/m$^2$ of BSA [6R]-5,10-methylenetetrahydrofolate, followed by c) optionally administering one IV bolus containing 5-1000 mg/m² of BSA [6R]-5,10-methylenetetrahydrofolate before the end of Day 1, followed by d) on Day 2, administering an IV bolus containing 10-1000 mg/m² of BSA 5-FU, or an analog or prodrug thereof, followed, either simultaneously, or after a period of 10 min-4 hours, by e) optionally administering one or more IV boluses each containing 5-1000 mg/m² of BSA [6R]-5,10-methylenetetrahydrofolate, wherein step b) is optionally repeated up to 4 times on Day 1 with an interval of 10 min-60 min between each bolus being administered, and wherein step e) is optionally repeated up to 4 times on Day 2 with an interval of between 10 min-60 min between each bolus being administered, and wherein all steps a)-e) are optionally repeated every 2 weeks for up to eight (8) cycles, or up to sixteen (16) weeks; and wherein the 5-FU analog or prodrug is a fluorinated pyrimidine base selected from the group consisting of capecitabine (Xeloda), N4-pentyloxycarbonyl-5'-deoxy-5-fluorocytidine, tegafur (ftorafur), 5-fluoro-pyrimidinone, UFT, doxifluridine, 2'-deoxy-5 fluorouridine, 5'-deoxy-5-fluorouridine, 1-(2'-oxopropyl)-5-FU, alkyl-carbonyl-5-FU, BOF-A2, and S-1 (TS-1).

2. The method according to claim 1, wherein the solid tumor is a cancer form selected from colon cancer, stomach cancer, breast cancer, bowel cancer, gallbladder cancer, lung cancer including adenocarcinoma, colorectal cancer (CRC) including metastatic CRC, head and neck cancer, liver cancer, osteosarcoma and pancreatic cancer.

3. The method according to claim 2, wherein the solid tumor is a colorectal cancer (CRC) including metastatic CRC.

4. The method according to claim 1, wherein the solid tumor is a colorectal cancer (CRC) including metastatic CRC.

5. The method according to claim 1, wherein step a) is preceded by administering one or more anticancer drugs on Day 1, either as an IV bolus or as an infusion over a period of 1-4 hours.

6. The method according to claim 5, wherein the anticancer drug is selected from oxaliplatin, irinotecan (CPT11) and bevacizumab (Avastin).

7. The method according to claim 1, wherein at least two boluses of [6R]-5,10-methylenetetrahydrofolate are administered on Day 1 under step b).

8. The method according to claim 7, wherein up to four boluses of [6R]-5,10-methylenetetrahydrofolate are administered with an interval of 20-30 min between each bolus.

9. The method according to claim 1, wherein at least two boluses of [6R]-5,10-methylenetetrahydrofolate are administered on Day 2 under step e).

10. The method according to claim 9, wherein up to four boluses of [6R]-5,10-methylenetetrahydrofolate are administered with an interval of 20-30 min between each bolus.

11. The method according to claim 1, wherein the [6R]-5,10-methylenetetrahydrofolate is employed as a solid form which is soluble in water, including a lyophilisate or a salt, optionally stabilized by one or more suitable excipients and/or antioxidants including citric acid or ascorbic acid or salt forms thereof.

12. The method according to claim 1, wherein the [6R]-5,10-methylene-tetrahydrofolate has a diastereomeric purity of >98% d.e.

13. The method according to claim 1, wherein the 5-FU analog or prodrug is a fluorinated pyrimidine base selected from the group consisting of capecitabine (Xeloda), N4-pentyloxycarbonyl-5'-deoxy-5-fluorocytidine, tegafur (ftorafur), 5-fluoro-pyrimidinone, UFT, doxifluridine, 2'-deoxy-5 fluorouridine, 5'-deoxy-5-fluorouridine, 1-(2'-oxopropyl)-5-FU, alkyl-carbonyl-5-FU, BOF-A2, and S-1 (TS-1).

14. A method for preventing or retarding the progression in a human of solid tumors, including cancer, which method comprises performing and repeating steps a) to e) according to claim 1 over a total treatment period of at least 8 weeks.

15. The method according to claim 14, whereby steps a) to e) are performed and repeated over a total treatment period of at least 16 weeks, and whereby no statistically significant progression of said solid tumors is observed between 8 and 16 weeks after initializing treatment.

* * * * *